United States Patent [19]
Thomason

[11] Patent Number: 5,149,792
[45] Date of Patent: Sep. 22, 1992

[54] PLATELET-DERIVED GROWTH FACTOR B CHAIN ANALOGS

[75] Inventor: Arlen R. Thomason, Thousand Oaks, Calif.

[73] Assignee: Amgen Inc., Thousand Oaks, Calif.

[21] Appl. No.: 454,794

[22] Filed: Dec. 19, 1989

[51] Int. Cl.$^5$ .................... C07K 13/00; A61K 37/36
[52] U.S. Cl. ................................................. 530/399
[58] Field of Search .................. 530/399; 435/69.1; 514/12

[56] References Cited
PUBLICATIONS

Collins et al. *Nature* 316:748–749 (1985).
Chambers et al. *EMBO J.* 5(6):1221–1227 (1986).

Primary Examiner—David L. Lacey
Assistant Examiner—Shelly J. Guest
Attorney, Agent, or Firm—Julia E. Abers

[57] ABSTRACT

Novel platelet-derived growth factor (PDGF) analogs are provided in accordance with the present invention. Also provided is a method for the production of homogeneous quantities of these novel analogs. The novel analogs of the present invention, when refolded, have substantially the same biological activity as naturally occurring PDGF $B_{109}$. The method of the present invention employs the use of a stop codon on the c-sis gene, or other coding sequence for a precursor protein of PDGF $B_{109}$, or analogs thereof, at a position corresponding to a location from about amino acid 111 to about amino acid 160. The method of the present invention results in the production of relatively large homogeneous quantities of recombinant PDGF B analogs from high expression host cells, such as *E. coli*.

4 Claims, 7 Drawing Sheets

```
Ser-Leu-Gly-Ser-Leu-Thr-Ile-Ala-Glu-Pro-Ala-Met-Ile-Ala-Glu-Cys-Lys-Thr-Arg-Thr-
              5              10              15              20
      total PDGF
|————————————————————————————————·····——————————————|
|————————————S73——————————————||————S25————|
|————————————T43———————————————————··········|
|——————————————————————————··········|   |T34|

Glu-Val-Phe-Glu-Ile-Ser-Arg-Arg-Leu-Ile-Asp-Arg-Thr-Asn-Ala-Asn-Phe-Leu-Val-Trp-
          25              30              35              40
   total PDGF
|S25|
   |————————————————S82————————————————————|
      |————T34————||————————T48————————|

Pro-Pro-Cys-Val-Glu-Val-Gln-Arg-Cys-Ser-Gly-Cys-Cys-Asn-Asn-Arg-Asn-Val-Gln-Cys-
          45              50              55              60
                              S49                        ||S61
|······——————————||————————————————|     ||————|
       T48           ||    T2     ||  T9
                                  ||

Arg-Pro-Thr-Gln-Val-Gln-Leu-Arg-Pro-Val-Gln-Val-Arg-Lys-Ile-Glu-Ile-Val-Arg-Lys-
          65              70              75              80
              S61                            ··········|| S63
|T9||—————————T33—————————————||———T27———|

Lys-Pro-Ile-Phe-Lys-Lys-Ala-Thr-Val-Thr-Leu-Glu-Asp-His-Leu-Ala-Cys-Lys-Cys-Glu-
          85              90              95              100
      S63                              S45
|———T21———||————————T31————||······——|      |T21|
                                              |—T22—

Thr-Val-Ala-Ala-Ala-Arg-Pro-Val-Thr-Arg-Ser-Pro-Gly-Gly-Ser-Gln-Glu-Gln-Arg
          105             110             115
      S39
|————————————·····————————————————————|
      S43
|——————————————|
      T21
|—————————·····—|
          T22
|—————————————————————————······|
```

```
            10                  30                  50
    CTAGAAGGAGGAATAACATATGTCTCTGGGTTCGTTAACCATTGCGGAACCGGCTATGAT
1   -----+---------+---------+---------+---------+---------+      60
    TTCCTCCTTATTGTATACAGAGACCCAAGCAATTGGTAACGCCTTGGCCGATACTA
                 MetSerLeuGlySerLeuThrIleAlaGluProAlaMetIl
                 1
            70                  90                 110
    TGCCGAGTGCAAGACACGAACCGAGGTGTTCGAGATCTCCCGGCGCCTCATCGACCGCAC
61  ---------+---------+---------+---------+---------+---------+  120
    ACGGCTCACGTTCTGTGCTTGGCTCCACAAGCTCTAGAGGGCCGCGGAGTAGCTGGCGTG
    eAlaGluCysLysThrArgThrGluValPheGluIleSerArgArgLeuIleAspArgTh
     14
            130                 150                170
    CAATGCCAACTTCCTGGTGTGGCCGCCCTGCGTGGAGGTGCAGCGCTGCTCCGGCTGTTG
121 ---------+---------+---------+---------+---------+---------+  180
    GTTACGGTTGAAGGACCACACCGGCGGGACGCACCTCCACGTCGCGACGAGGCCGACAAC
    rAsnAlaAsnPheLeuValTrpProProCysValGluValGlnArgCysSerGlyCysCy
     34
            190                 210                230
    CAACAACCGCAACGTGCAGTGCCGGCCCACCCAGGTGCAGCTGCGGCCAGTCCAGGTGAG
181 ---------+---------+---------+---------+---------+---------+  240
    GTTGTTGGCGTTGCACGTCACGGCCGGGTGGGTCCACGTCGACGCCGGTCAGGTCCACTC
    sAsnAsnArgAsnValGlnCysArgProThrGlnValGlnLeuArgProValGlnValAr
     54
            250                 270                290
    AAAGATCGAGATTGTGCGGAAGAAGCCAATCTTTAAGAAGGCCACGGTGACGCTGGAGGA
241 ---------+---------+---------+---------+---------+---------+  300
    TTTCTAGCTCTAACACGCCTTCTTCGGTTAGAAATTCTTCCGGTGCCACTGCGACCTCCT
    gLysIleGluIleValArgLysLysProIlePheLysLysAlaThrValThrLeuGluAs
     74
            310                 330                350
    CCACCTGGCATGCAAGTGTGAGACAGTGGCAGCTGCACGGCCTGTGACCCGAAGCCCGGG
301 ---------+---------+---------+---------+---------+---------+  360
    GGTGGACCGTACGTTCACACTCTGTCACCGTCGACGTGCCGGACACTGGGCTTCGGGCCC
    pHisLeuAlaCysLysCysGluThrValAlaAlaAlaArgProValThrArgSerProGl
     94
            370         380
    GGGTTCCCAGGAGCAGCGATAAG
361 ---------+---------+---
    CCCAAGGGTCCTCGTCGCTATTCTTAA
    yGlySerGlnGluGlnArg
     114                119
```

FIG. 3

PLATELET-DERIVED GROWTH FACTOR B CHAIN ANALOGS

Human platelet-derived growth factor (PDGF) is believed to be the major mitogenic growth factor in serum for connective tissue cells. The mitogenic activity of PDGF has been documented in numerous studies, wherein PDGF has been shown to positively affect mitogenesis in arterial smooth muscle cells, fibroblast cell lines, and glial cells. Deuel et al, *J. Biol. Chem.*, 256(17), 8896–8899 (1981). See also, e.g., Heldin et al, *J. Cell Physiol.*, 105, 235 (1980) (brain glial cells); Raines and Ross, *J. Biol. Chem.*, 257, 5154 (1982) (monkey arterial smooth muscle cells). PDGF is also believed to be a chemoattractant for fibroblasts, smooth muscle cells, monocytes, and granulocytes. Because of its apparent abilities to both induce mitogenesis at the site of connective tissue wounds, and to attract fibroblasts to the site of such wounds, PDGF is thought to have particular potential for therapeutic use in the repair of injured, or traumatized, connective tissues.

PDGF was initially described by Ross et al, *Proc. Natl. Acad. Sci. USA*, 71, 1207–1210 (1974), as a factor found in whole blood serum (but not platelet-poor serum) which is capable of supporting the growth of fibroblasts in culture. PDGF was subsequently isolated from platelets and from serum, with the native unreduced PDGF being identified as a 27–35 kd mw dimeric protein. Reduction of PDGF was found to yield two or more smaller bands on gels, in a molecular weight range of 10–18 kd. These smaller bands were believed to represent two smaller, dissimilar monomeric subunits of approximately 18 kd and 16 kd molecular weights called, respectively, the "A" and "B" subunits, or alternatively, PDGF A chain and PDGF B chain. The amino acid sequences of the two subunits of PDGF have since been described, with the amino acid sequence of the PDGF B chain being identified as being more than 90% homologous with the predicted protein product of v-sis, the oncogene contained within the oncogenic simian sarcoma virus (SSV). Doolittle et al, *Science*, 221, 275–276 (1983), and Waterfield et al, *Nature*, 304, 2810–2814 (1983). The A chain has been found to be approximately 60% homologous to the B chain.

The PDGF B found in human platelets has been further identified as a 109 amino acid cleavage product of a 241 amino acid precursor polypeptide, which is encoded by c-sis, the human counterpart of the v-sis gene. Johnsson et al, *EMBO Journal*, 3(5), 921–928 (1984). The Johnsson et al sequencing data also confirmed the high degree of homology of the predicted amino acid sequence of the v-sis gene product, $p28^{sis}$, with the actual amino acid sequence of the B chain of PDGF. The homology of the PDGF B chain to the v-sis gene product begins at amino acid 67 of $p28^{sis}$, a serine residue, and continues for 109 amino acids to a threonine residue at amino acid 175. Johnsson et al, ibid. This 109 amino acid homologous sequence also coincides with the 109 amino acid cleavage product of the c-sis encoded precursor protein, believed to be the mature form of PDGF in humans. Homology with the c-sis encoded precursor protein begins at amino acid 82 of the 241 amino acid precursor protein and continues for 109 amino acids.

PDGF is believed to be biologically active only in dimeric form. These biologically active PDGF dimers can take the form of a PDGF A-B heterodimer, a PDGF B-B homodimer, or a PDGF A-A homodimer. Hannink et al, *Mol. Cell. Biol.*, 6, 1304–1314 (1986). Each monomeric subunit of the biologically active dimer, irrespective of whether it is an A chain monomer or a B chain monomer, contains eight cysteine residues. Some of these cysteine residues form interchain disulfide bonds which hold the dimer together.

The 109 amino acid v-sis homologous sequence (PDGF $B_{109}$), identified by Johnsson et al as being the mature form of PDGF B, has been used in recombinant technology employing yeast and other eucaryotic host cell systems to obtain active recombinant PDGF (rPDGF). (U.S. Pat. No. 4,766,073 ("Murray et al I"), yeast host cells.) The use of a coding sequence encoding PDGF $B_{109}$ provides two advantages over the use of the entire c-sis coding sequence: (1) the 109 amino acid coding sequence facilitates the recombinant production of a protein such as PDGF B, because it is easier to manipulate than the longer c-sis coding sequence; and, (2) the 109 amino acid coding sequence results in a recombinant product which is closer in structure to the mature form of PDGF B, and, thus, may require less processing by the human subject being treated by a therapeutic compound containing rPDGF B. It has been suggested that further deletion of carboxy and/or amino terminus amino acids, resulting in still smaller potentially biologically active PDGF B analogs, may have even broader therapeutic utility (U.S. Pat. No. 4,845,075 ("Murray et al II")), but the therapeutic efficacy of these truncated forms has not been demonstrated.

PDGF $B_{109}$ can be prepared by recombinant technology using any one of a number of starting materials to derive the necessary coding sequences. For example, one can modify the commonly available v-sis gene to obtain the human counterpart c-sis gene, and then transfect the desired host cell following insertion of a stop codon at amino acid 110. Alternatively one can either use c-sis as a starting material, or synthesize the 109 amino acid coding sequence. It is still further possible to utilize a combination of these methods, for example, such as described in Murray et al I. In any case, a stop codon must still be placed at amino acid position 110 on the coding sequence. Otherwise, the replication system of the host cell will translate past the 109 amino acid codon until a naturally occurring stop codon is reached, producing a protein which contains the amino acid sequences of the remaining c-sis encoded protein (where a vector incorporating the c-sis gene is used) or vector encoded protein (where a synthetic gene is used).

Use of the more highly evolved eucaryotic host cell systems and yeast host cell systems for the recombinant production of PDGF B typically results in the secretion of biologically active rPDGF B in relatively low levels. However, the processing systems within these more highly evolved host cells generate recombinant rPDGF B homodimer product which has been processed in any number of ways by the natural biological processes of the host cell, such as by glycosylation and/or proteolytic cleavage. This is particularly true in the case of mammalian host cells. As a result, the precise composition of the recombinant product cannot be accurately predicted, or, in many cases, accurately controlled.

Procaryotic host cell systems, such as *E. coli*, on the other hand, produce a more easily controlled and defined product, due to the relative lack of biological processing pathways that exist at the lower evolutionary scale occupied by these host cells. Procaryotic host cell systems also produce much greater amounts of the desired recombinant product. The tradeoff with higher expression systems is that, in return for obtaining higher yields of recombinant product, the recombinant protein must be isolated from inclusion bodies. This typically requires refolding of the denatured protein in order to generate biologically active product. However, recently developed refolding methods, such as described in copending, commonly assigned U.S. patent application Ser. No. 451,485, which is incorporated herein by reference, have increased the desirability of producing rPDGF B in high expression host cell systems.

Nevertheless, production of PDGF $B_{109}$ in *E. coli* has, at least in some instances, surprisingly been found to exhibit a stop codon "read through" problem. In other words, the host cell expression system may read through the stop codon at position 110 some of the time, thus expressing a longer product than the desired PDGF $B_{109}$ end product. For example, when the stop codon UGA is placed at position 110 of the c-sis gene, it has been found that the amino acid selenocysteine is inserted at this position during "read through". Insertion of selenocysteine during "read through" of naturally occurring UGA codons in several other proteins has also been reported. Zinoni et al, *Proc Natl. Acad. Sci. U.S.A.*, 84, 3156-3160 (1987); Chambers et al, *EMBO J.*, 5, 1221-1227 (1986); Sukenaga et al, *Nucleic Acids Res.*, 15, 7178 (1987). Partial "read through" has also been observed, to a lesser extent, when UAG or UAA stop codons are placed at position 110 of the c-sis gene. The "read through" problem causes *E. coli* host cells to produce a heterogeneous mixture of PDGF $B_{109}$ combined with a longer form of PDGF B. This, in turn, requires additional separation step(s) to be performed in order to obtain a homogeneous product.

For therapeutic and commercial purposes, it would be desirable to economically obtain significant quantities of a reliable, biologically active form of PDGF B. The inability of high expression procaryotic host cell systems to produce rPDGF B in a homogeneous form, significantly increases the expense of generating a homogeneous product through the added cost of the requisite separation step(s).

It is an object of the present invention to provide a highly expressed, homogeneous rPDGF B product which is biologically active and which closely resembles naturally occurring PDGF B.

SUMMARY OF THE INVENTION

Novel rPDGF B analogs are provided in accordance with the present invention. Also provided is a method for the homogeneous production of significant quantities of these novel analogs. The method of the present invention employs a novel coding sequence wherein a stop codon is placed on the c-sis gene, or other coding sequence for a precursor protein of PDGF B, or analogs thereof, at a position corresponding to a location from about amino acid 111 to about amino acid 160. The method of the present invention results in the production of relatively large homogeneous quantities of rPDGF B analogs from high expression host cells, such as *E. coli*. The rPDGF B analogs produced by the method of the present invention exhibit biological activity comparable to that exhibited by naturally occurring PDGF $B_{109}$.

BRIEF DESCRIPTION OF THE DRAWINGS

FIG. 1 is a diagram of the amino acid sequencing data derived from the analysis of mammalian rPDGF B.

FIG. 2 is a Coomassie Brilliant Blue-stained electrophoretic gel showing the relative migration of mammalian rPDGF B compared with *E. coli* rPDGF $B_{109}$ and rPDGF $B_{119}$.

FIG. 3 is a diagram of the coding sequence used to express rPDGF $B_{119}$ in *E. coli* expression vector pCFM1156, as set forth in Example 1.

DETAILED DESCRIPTION OF THE INVENTION

Figure 4:
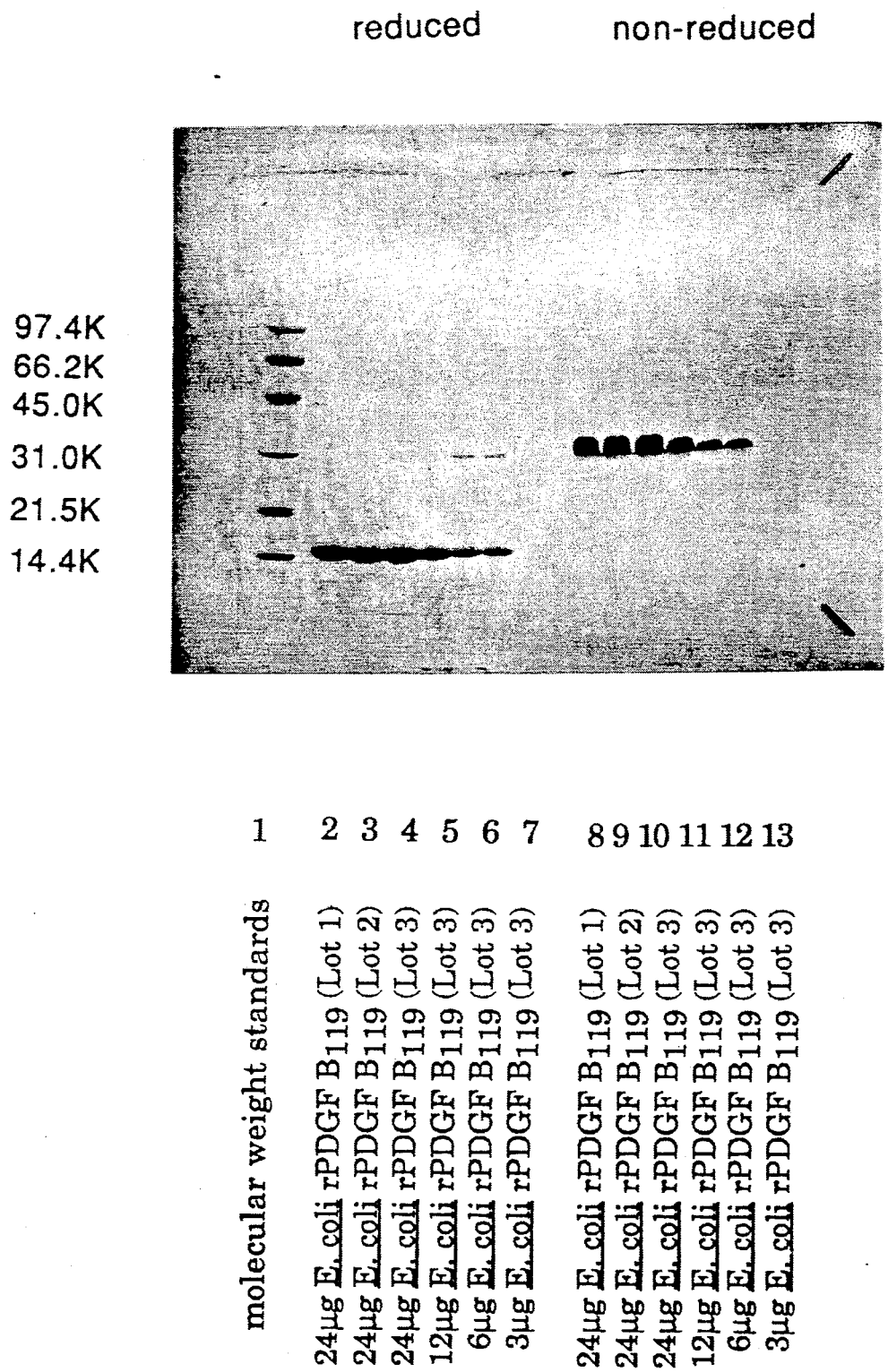
FIG. 4 is a Coomassie Brilliant Blue-stained electrophoretic gel showing the migration of *E. coli* rPDGF $B_{119}$ from various lots produced in accordance with the present invention.

The present invention provides novel rPDGF B analogs. These analogs are 110-159 amino acids in length, and have the same amino acid sequence as a portion of PDGF $B_{109}$ precursor protein or PDGF $B_{109}$ precursor protein analog.

The present invention further provides a method for the homogeneous production of commercially useful amounts of such novel rPDGF B analogs from high expression host cell systems such as *E. coli*. The method of the present invention is carried out by transfecting or transforming a selected host cell with a novel coding sequence. The novel coding sequence employs the c-sis gene, or other coding sequence for PDGF $B_{109}$ precursor protein or analogs thereof, wherein a stop codon is placed at a position corresponding to about amino acid 111 to about amino acid 160.

In order to aid in the understanding of the present invention, the following terms, as used herein, have the definitions designated below.

Unless otherwise specified, PDGF B is any combination of PDGF B monomers and/or dimers, including analogs thereof, reduced or unreduced, biologically active, or inactive, recombinant or otherwise. The term "PDGF B" is specifically intended to include PDGF B analogs having one or more modifications to the number and/or identity of amino acid sequences of naturally occurring PDGF $B_{109}$. PDGF B analogs are biologically active or capable of being made biologically active by refolding techniques or other similar mechanical manipulations.

The term "biologically active PDGF B" means PDGF B having substantially the same mitogenic activity and/or chemotactic activity as naturally occurring PDGF $B_{109}$.

"Precursor protein" refers to the 241 amino acid c-sis-encoded precursor protein of PDGF $B_{109}$.

The term "precursor protein analog" refers to a precursor protein having one or more modifications to the number and/or identity of amino acid sequences of the 241 amino acid encoded by the c-sis gene. Precurosr protein analogs, like precursor protein, are encoded by precursor protein coding sequences.

As used herein, the term "precursor protein coding sequence" means the c-sis gene or any coding sequence which codes for the 241 amino acid c-sis encoded PDGF $B_{109}$ precursor protein or analogs thereof. Although the precursor protein coding sequence may have one or more modifications to the number and/or identity of codons in the naturally occurring c-sis gene, the precursor protein coding sequence: (1) is capable of hybridizing to the c-sis gene; or, (2) but for the degeneracy of the genetic code, would hybridize to the c-sis gene and/or (1) above. Most commonly, a precursor protein coding sequence will contain preferred codons for expression in the selected host cell system.

In the numbering system employed herein, amino acid number 1 is designated as the amino terminal serine of mature platelet PDGF B as determined by Johnsson et al, ibid. This position corresponds to residue 82 of the 241 amino acid precursor protein. Amino acids preceding serine number 1 in the c-sis-encoded precursor protein are designated by negative numbers. Amino acids following serine number 1 are numbered sequentially, such that the 241st amino acid of the precursor protein is designated amino acid 160.

It is preferred to obtain a homogeneous PDGF B product from high expression procaryotic host cells which would most closely resemble the naturally occurring mammalian PDGF B. In order to identify preferred potential alternative sites for placement of the stop codon on the precursor protein coding sequence for insertion into a procaryotic host cell, the entire 241 amino acid c-sis gene was first inserted into an expression vector and used to transfect mammalian Chinese hamster ovary (CHO) cells. The resulting secreted protein products were then purified and separated chromatographically to determine the carboxy termini end points of the proteins as processed by the CHO cells. It was found, as more fully described in the examples which follow, that the two predominant PDGF B protein products secreted by the CHO cells were terminated after amino acid 109 and after amino acid 119. In addition, at least two other PDGF B analogs were processed by proteolytic cleavage in a range of after about amino acid 126 to after about amino acid 136. Based on probable proteolytic cleavage sites, the carboxy termini of these two additional PDGF analogs were estimated to end after arginine residues; i.e., at about amino acid 126, 130, 133, 135, or 136.

Preferably, the method of the present invention is carried out by transfecting or transforming a host cell with a precursor protein coding sequence wherein a stop codon has been placed at a position on the precursor protein coding sequence from about amino acid 111 to about amino acid 137. More preferably, the stop codon is placed at a position from about amino acid 120 to about amino acid 137. Still more preferably, the stop codon is placed at a position selected from the group consisting of amino acid 120, amino acid 127, amino acid 131, amino acid 134, amino acid 136, and amino acid 137. Most preferably, a coding sequence employing a stop codon at amino acid position 120 is used to carry out the method of the present invention. The method of the present invention results in the production of a novel analog of PDGF B having a length of about 110 to about 159 amino acids. The most preferred positioning of the stop of the stop codon results in the production of PDGF B119.

The method of the present invention can generally be carried out using a modification of any one of a number of methods for the recombinant production of PDGF B known to those skilled in the art. For example, one can first modify the v-sis gene to obtain the human counterpart c-sis, or use c-sis as a starting material, and then transfect the desired host cell following placement of a stop codon at any of amino acid positions 111 to 160. The stop codon is preferably placed in the c-sis or modified v-sis precursor protein coding sequence by site-directed mutagenesis of a pre-existing codon.

Alternatively one can either synthesize the precursor protein coding sequence, or first cut back the c-sis gene or modified v-sis gene, at an appropriate restriction site near the carboxy terminus, and then rebuild the carboxy terminus of the precursor protein coding sequence to the desired end position (about 111 to about 160) using preferred codons for the particular vector and host cell systems being employed. The c-sis gene or modified v-sis gene can also be cut back at an appropriate restriction site near the amino terminus, with the amino terminus being built back to the desired starting position (preferably amino acid 1), again using preferred codons for the selected vector and host cell systems. Regardless of whether naturally occurring or synthesized starting materials, or a combination thereof, are used, a stop codon must be placed after the desired carboxy terminal amino acid of the precursor protein coding sequence; i.e., at any one of amino acid positions at about 111 to about 160.

In the preferred method for carrying out the present invention, the v-sis gene is modified to obtain the c-sis gene, after which, or concurrently therewith, a stop codon is placed at the desired location of the modified gene, in accordance with the teachings of the present invention. The c-sis precursor protein coding sequence containing the stop codon is then inserted into a vector, which is used to transfect the desired procaryotic host cell.

More preferably, the precursor protein coding sequence used in the method of the present invention is an analog of the c-sis gene. The c-sis analog precursor protein coding sequence may be constructed to contain preferred codons for expression in an *E. coli* host cell. The analog of the c-sis gene may obtained by both site-directed mutagenesis and ligation of the c-sis gene with synthetic carboxy and amino termini following proteolytic cleavage of the existing termini at appropriate proteolytic cleavage sites.

The v-sis gene provides an excellent starting material for obtaining a precursor protein coding sequence for use in the present invention. For example, in the region coding for amino acids 1-119, there are only five amino acid differences between the protein encoded by the v-sis gene and the c-sis encoded PDGF $B_{109}$ precursor protein. Two of these five amino acids in the v-sis gene can be altered by in vitro mutagenesis techniques to generate a DNA sequence coding for a protein in which the two amino acids are the same as the corresponding residues in the PDGF $B_{109}$ precursor protein. A number of methods for in vitro mutagenesis of DNA can be utilized for introducing the desired changes in codons 101 and 107. Such methods are well know to those skilled in the art. For example, the method of Eckstein and co-workers (Taylor et al, *Nucl. Acids Res.*, 13, 8764–8785 (1985); Nakamaye and Eckstein, *Nucl. Acids*

Res., 14, 9679–9698 (1986)), as described in the instruction booklet for the Amersham (Arlington Heights, Ill.) "Oligonucleotide-Directed In Vitro Mutagenesis System" kit, is particularly useful in converting the isoleucine reside at amino acid 101 to a threonine residue, and the alanine residue at amino acid 107 to a proline residue.

Following in vitro mutagenesis of amino acids 101 and 107, the altered v-sis DNA may then be cut back at the amino terminus with the restriction enzyme BglII, which cuts at a position corresponding to amino acid 24. The upstream portion of the gene, including the first 24 amino acids, may be restored by ligation of the downstream, BglII-cut mutagenized v-sis DNA with a synthetic DNA fragment encoding: (1) an ATG translation initiation codon; (2) a serine residue at amino acid 1; and, (3) the remainder of the first 24 amino acids of the c-sis encoded precursor protein. In this way, two of the other three variant amino acids, i.e., the serine residue at amino acid 6 and the valine residue at amino acid 7, will be converted to the human PDGF B forms (threonine and isoleucine, respectively), with the upstream precursor amino acids encoded by v-sis being removed.

Cutting back from the carboxy terminus in a similar manner enables replacement of the carboxy terminus with a synthetic fragment which simultaneously alters amino acid 114 and replaces amino acid 120 with a stop codon. Preferably, the mutagenized v-sis DNA is cut with the restriction enzyme SmaI, which cuts at a position corresponding to amino acid 112. A synthetic DNA fragment coding for amino acids 112–119 of the PDGF $B_{109}$ precursor protein, and a translation stop codon at position 120, may then ligated to the SmaI-cut mutagenized v-sis DNA. This synthetic DNA also encodes for a glycine residue, instead of a threonine residue, at amino acid 114, accomplishing the conversion of the fifth variant amino acid to the corresponding amino acid in the PDGF $B_{109}$ precursor protein.

The final DNA construct of this precursor protein coding sequence codes for amino acids 1–119 of PDGF B, plus an additional methionine residue at the N-terminus. This PDGF $B_{119}$ gene may then be ligated into an appropriate expression vector, such as pCFM1156, and then transformed or transfected into an appropriate host cell system, preferably a procaryote such as an E. coli host cell, with the N-terminal methionine being removed in vivo following synthesis in the host cell.

The preferred expression systems for the homogeneous production of the rPDGF B analogs of the present invention comprise procaryotic cell culture systems, preferably E. coli. In addition to the particular expression systems herein described, other systems are contemplated by the present invention and include, for example but without limitation, modification of the sites for protease cleavage, and/or use of an alternate leader sequence to increase the level of production from host cells of the rPDGF analogs of the present invention.

The biologically active homogeneous rPDGF B analogs produced by the method of the present invention can be used for the in vivo treatment of mammalian species by physicians and/or veterinarians. The amount of active ingredient will, of course, depend upon the severity of the conditions being treated, the route of administration chosen, and the specific activity of the rPDGF B analog, and will be determined by the attending physician or veterinarian. The amount of rPDGF B analog determined to produce a therapeutic response in a mammal is referred to as "PDGF B analog therapeutically effective" amount. Such therapeutically effective amounts are readily ascertained by one of ordinary skill in the art. Therapeutically effective amounts of rPDGF B analog for treating full and partial thickness dermal wounds are disclosed in copending, commonly assigned patent application Ser. No. 362,622, which is incorporated herein by reference.

The following examples are provided to aid in the understanding of the present invention, the true scope of which is set forth in the appended claims. It is understood that modifications can be made in the procedures set forth, without departing from the spirit of the invention.

EXAMPLE 1

Purification and Separation of CHO-produced rPDGF B

The c-sis gene, containing a naturally occurring stop codon at amino acid 161, was cloned and expressed in CHO cells as described in detail in International Patent Application No. PCT/US88/0070, with the resulting rPDGF B being purified and separated as set forth below.

The rPDGF B from the conditioned media of mammalian CHO-pDSVE/c-sis cells was purified in four steps, then concentrated and diafiltered. In the first step, a strong cation exchange resin, Biocryl BPA-2100, was added to the filtered conditioned media at a level of 0.125% (vol. 10% suspension/vol. medium). After stirring to allow binding of the rPDGF B protein product to the resin, the product-resin complex was recovered by continuous flow centrifugation. The pellet was then washed with approximately 8 volumes (relative to the wet weight of the pellet) of a buffer comprising 10% ethanol/10 mM Tris.HCl, pH 7.7 and recovered by centrifugation. The pellet was resuspended in two volumes of the same buffer, after which an equivalent volume of 95% ethanol was added. This suspension was stored a $-20°$ C.$\pm 10°$ C. prior to further processing.

The resin suspension was centrifuged, and the pellet was resuspended in 0.1 M NaCl/20 mM Tris HCl, pH 7.7 at controlled room temperature. After a suspension was obtained, 10% (w/v) sodium N-lauroylsarcosine was added to a final concentration of 1% (w/v). The suspension was then mixed for at least 30 minutes, after which it was subjected to centrifugation to separate the resin (pellet) from the product (now in the supernatant). The resin was then re-extracted as before, using one-third of the volume of the sodium N-lauroylsarcosine extractant, to obtain any residual product which may have been occluded in the pellet after the first extraction.

The pooled supernatants from the resin extraction steps were brought to pH 2.7$\pm$0.1 with hydrochloric acid (HCl). 1.05 volumes of 95% ethanol were then added, and a slight precipitate was removed by centrifugation.

The supernatant from the previous step was applied to a sulphoxyethyl (SE)-cellulose column previously equilibrated with 50% ethanol/5 mM HCl. At acid pH, N-lauroylsarcosine was uncharged, and thus passed through the column, whereas the product, rPDGF B, being cationic, bound to the column matrix. The column was washed with 50% ethanol/5 mM HCl to remove residual N-lauroylsarcosine, then with 20 mM $NaPO_4$, pH 7.5, to bring it to neutral pH, and finally with 10 mM Tris.HCl, pH 7.7. The rPDGF B product was eluted with 0.5 M NaCl/10 mM Tris.HCl, pH 7.7.

Two and one-half volumes of water for injection were added to the rPDGF B solution, followed by 2.5 volumes of 3.0 M $(NH_4)_2SO_4$. The product was then applied to a Phenyl-Sepharose ® (Pharmacia, Uppsala, Sweden) column previously equilibrated with 5% ethanol/1.25 M $(NH_4)_2SO_4$/50 mM $NaPO_4$, pH 7.5. After loading with the product, the column was washed with the latter buffer. The rPDGF B product was eluted from the column using a linear gradient decreasing in ammonium sulfate and increasing in ethanol. The starting buffer was the same as the washing buffer, and the limit buffer was 30% ethanol/50 mM $NaPO_4$, pH 7.5. Fractions from this column were analyzed by SDS-PAGE under non-reducing conditions. Those fractions containing product free of other protein contaminants were pooled.

The pooled fractions from the previous step were brought to pH 4.0±0.1 with 1 N HCl, and then concentrated over an Amicon YM ® 10 (Amicon Inc., Danvers, Mass.) ultrafiltration membrane to an absorbance at 280 nm (1 cm light path) of approximately 0.6. The product was then diafiltered with at least four volumes of 10 mM ammonium acetate/0.15 M NaCl, pH 4.0 The product solution was then diluted with this solution to an absorbance a 280 nm (1 cm light path) of 0.24±0.04 which is the equivalent of 0.5 mg rPDGF B/mL.

EXAMPLE 2

Determination of Primary Structure of rPDGF B Secreted by CHO Cells

In order to determine the positions at which mammalian cells may process the 241 amino acid c-sis-encoded precursor protein to PDGF $B_{109}$, the structure of the secreted, processed recombinant protein product was analyzed by analytical gel electrophoresis and by protein sequencing.

Amino Acid Sequence Analysis

The amino acid sequence of rPDGF B purified from the conditioned media of CHO-pDSVE/c-sis cells was determined by a combination of sequence analysis of the intact rPDGF B, and sequence analysis of tryptic and SV8 protease peptides obtained by digestion of reduced rPDGF B which had been derivatized with 4-vinyl pyridine. The sequence determinations were performed using 470A and 477A sequencers (Applied Biosystems, Inc., Foster City, Calif.). The results are summarized below and in FIG. 1.

Intact rPDGF B was sequenced for 26 cycles. The major sequence identified in this analysis begins with rPDGF B amino acid 1 and is indicated by the upper lines labeled "total PDGF" in FIG. 1. This sequence corresponds to that expected for rPDGF B from the DNA sequence. The preparation used for this sequencer run was not alkylated, so the cysteine at cycle 16 could not be detected. Unalkylated cysteine is not easily identified by sequence analysis. Minor sequences were observed corresponding to fragments beginning at amino acids 33 and 80 of the rPDGF B sequence. These minor amino termini are similar to those observed from human platelets (Johnsson et al, ibid) and are due to internal cleavages produced during processing of the protein.

Peptide fragments were isolated following separate trypsin and SV-80 protease digestions of rPDGF B which had been reduced and alkylated with 4-vinyl pyridine. The reduction was necessary because unreduced rPDGF B is not digested by trypsin or SV-8 protease. Alkylation with 4-vinyl pyridine allowed detection of cysteines by the sequencer.

The combination of amino terminal sequence analysis of total rPDGF B and of amino terminal sequence analysis of tryptic and SV-8 peptides confirmed the protein sequence through residue 118. Carboxy terminal sequence analysis with carboxypeptidase P was employed to confirm residues 117 through 119. The data indicated that the major form of the rPDGF B protein preparation from the mammalian CHO cells is identical with the 119 amino acid residues shown in FIG. 1.

Analytical Gel Electrophoresis

Figure 2:
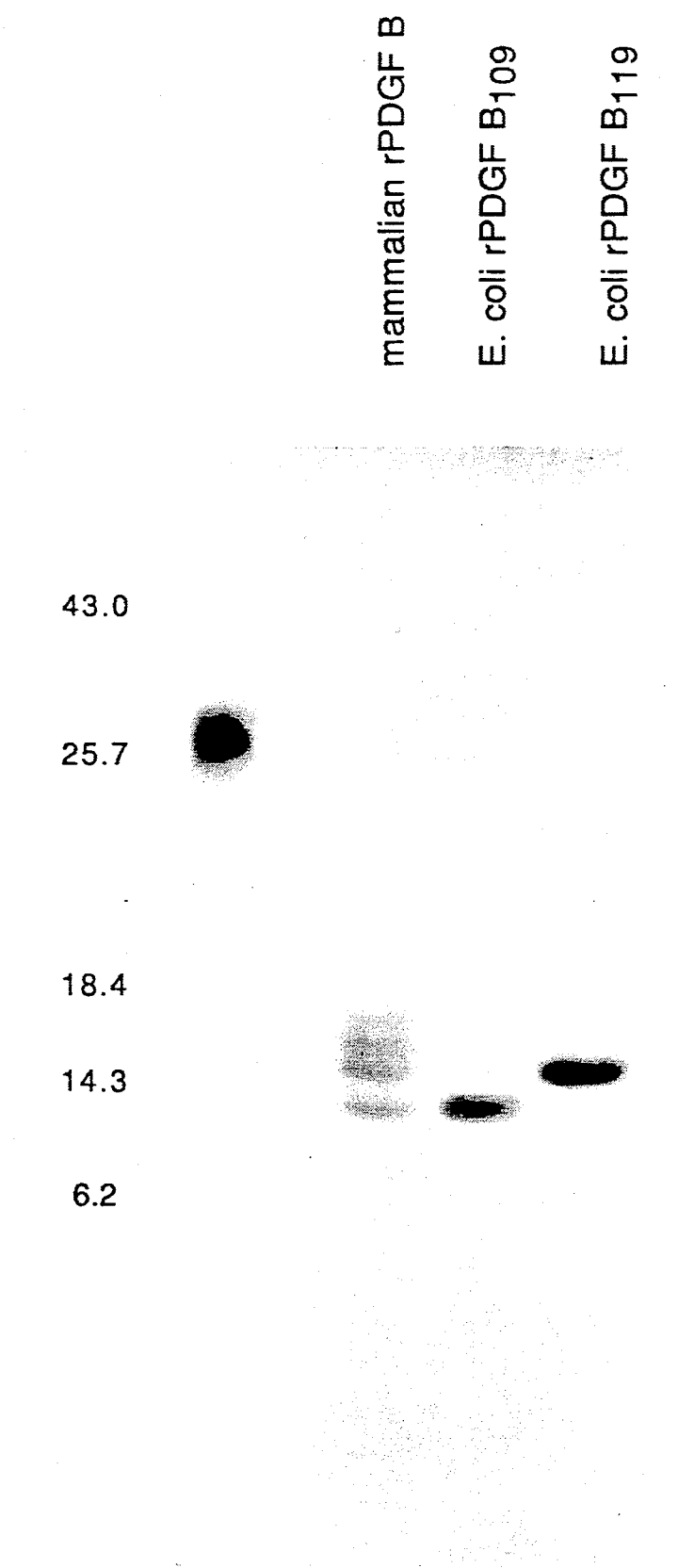

The rPDGF B product purified from the conditioned medium of mammalian CHO-pDSVE/c-sis cells, as described in Example 1, was electrophoresed on a 12% SDS-polyacrylamide gel. This technique allows the estimation of the length of polypeptides of unknown size when they are compared to appropriate protein standards of known size. The rPDGF B protein (10µg) produced by CHO-pDSVE/c-sis cells was electrophoresed both before and after reduction, and the gel was then stained with Coomassie Brilliant Blue. As can be seen in FIG. 2, lanes 1 and 2, this protein migrated considerably faster after reduction. Analysis of the reduced sample also revealed the presence of four major bands. The pattern is consistent with a structure for unreduced rPDGF B in which rPDGF B monomers of four different lengths are paired into disulfide dimers.

In order to obtain an accurate determination of the sizes of the four rPDGF B monomers secreted by CHO-pDSVE/c-sis cells, the electrophoretic mobilities of these polypeptides were compared to those of two rPDGF B proteins of known size, namely rPDGF $B_{109}$ and rPDGF $B_{119}$, produced using a bacterial expression system. These bacterially-produced rPDGF B proteins were obtained as described in Example 3, with the exception that, in one case, a coding sequence employing a stop codon at amino acid position 110, was employed to transfect the bacterial host cell. Due to the presence of a stop codon "read through" problem in the latter case, the resulting recombinant proteins (PDGF $B_{109}$ and PDGF $B_{160}$) had to be separated from the conditioned medium. The two bacterially-produced rPDGF B proteins chosen for use as standards against the mammalian recombinant product were specifically engineered to terminate at the carboxyl end with amino acids 109 and 119, based on the sequence analysis of PDGF B from human platelets (Johnsson et al, ibid) and rPDGF B from CHO-pDSVE/c-sis cells (described above).

Amino acid sequence analysis was performed as set forth in Example 2, and confirmed that these two bacterially produced proteins consisted of residues 1-109 and 1-119, respectively, of the PDGF $B_{109}$ precursor protein amino acid sequence. As shown in FIG. 2, lanes 2-4, the fastest migrating polypeptide in the reduced mammalian (CHO-pDSVE/c-sis) rPDGF B sample co-migrated with the *E. coli* rPDGF $B_{109}$ standard, while the next fastest migrating polypeptide in the mammalian sample co-migrated with the *E. coli* rPDGF $B_{119}$ standard. The two slowest migrating polypeptides in the mammalian sample migrated at positions consistent with lengths 5-20 amino acids longer than the 119 amino acid form. Basic amino acid residues are often the site of proteolytic cleavages. Examination of the amino acid sequences of the 241 amino acid PDGF $B_{109}$ precursor protein revealed basic amino acids at positions 126, 130, 133, 135, and 136. Cleavage at any one of these positions would yield PDGF B analogs having lengths 7-17 amino acids longer than the 119 amino acid form.

The amino acid sequencing and gel electrophoretic analyses together indicate that rPDGF B secreted by mammalian (CHO-pDSVE/c-sis) host cells is a mixture of dimers derived from four monomers, each of which has an amino terminus comprised of serine number 1 of the PDGF $B_{109}$ protein sequence. The most abundant of the four polypeptides has a carboxy terminus which ends at arginine number 119. One of the other of these polypeptides has a carboxy terminus consisting of threonine number 109. The remaining two polypeptides terminate at the carboxyl end with an amino acid 5-20 amino acids longer than the 119 amino acid form, most probably at arginine 126, arginine 130, arginine 133, arginine 135, or arginine 136.

EXAMPLE 3

Production of rPDGF $B_{119}$

A PDGF $B_{119}$-encoding precursor protein coding sequence, shown in FIG. 3, was constructed using the v-sis gene as a starting material.

Conversion of Amino Acids 101 and 107

One μg of the plasmid pC60, a clone of the simian sarcoma virus retroviral genome (Wong-Staal et al, *Science*, 213, 226-228 (1981), was digested with restriction endonucleases SalI and XbaI, with the resulting 1183 base pair fragment then being purified by electrophoretic separation in a low-melting temperature agarose gel, in accordance with the procedures described by Maniatis et al, *Molecular Cloning — A laboratory Manual*, Cold Spring Harbor Laboratory (1982). The purified fragment was then excised from the gel. At the same time, 0.2 μg of M13mp19 DNA was also digested with SalI and XbaI, with the large 7245 base pair band being similarly isolated from a low-melting temperature gel. Both excised gel slices were melted at 65° C., and then cooled to 37°. All of the gel with the 7245 base pair M13mp19 fragment and one fourth of the gel with the 1183 base pair v-sis fragment were mixed and ligated according to Struhl, *Biotechniques*, 3, 452-453 (1985). The ligated DNA was transformed into *E. coli* K12 strain TG1, and a clear plaque was selected and grown in liquid culture. The presence of the 1183 base pair v-sis fragment in the M13mp19 vector was confirmed by preparation of the RF form of the phage DNA and restriction map analysis. Messing et al, *Nucl. Acids Res.*, 9, 309-321 (1981).

The M13mp19/v-sis phage thus obtained was grown in liquid culture, and the single stranded DNA isolated. Messing et al, ibid. This DNA was used as a template for oligonucleotide-directed in vitro mutagenesis to convert the amino acids at residues 101 and 107 to the corresponding amino acids of PDGF B. I.e., the ATA codon coding for isoleucine 101 was converted to ACA (coding for threonine), and the GCT codon coding for alanine 107 was converted to CCT (coding for proline).

10 μg of the M13mp19/v-sis single-stranded DNA was annealed with 8 pmol of a phosphorylated oligonucleotide having the sequence:

5'GGTCACAGG̲CCGTGCAGCTGCCACTG̲TCTCACAC 3'

This sequence is homologous to nucleotides 4283 to 4316 of the v-sis gene (numbering system of Devare et al, hid). The underlined bases of the oligonucleotide denote the changes from the v-sis to the human PDGF B sequence. DNA synthesis was initiated on the mutant oligonucleotide, with the complete mutant strand being synthesized with the Klenow fragment of *E. coli* DNA polymerase I using thionucleotide triphosphates, followed by ligation with T4 DNA ligase. Any remaining single-stranded template M13mp18/v-sis DNA was removed by filtration on nitrocellulose filters. The non-mutant strand was nicked by incubation with restriction endonuclease III. The nicked non-mutant strand was then repolymerized with the deoxynucleotide triphosphates, using the mutant strand as a template. As a result, both DNA strands in the final product contained the desired mutations. The DNA was transformed into *E. coli* K12 strain TG1. Plaques were selected, grown in liquid culture, and the single-stranded DNA isolated. The DNA was sequenced by the method of Sanger et al, *Proc. Natl. Acad. Sci. U.S.A.*, 74, 5463-5467 (1977) to confirm that the desired mutants had been obtained.

Conversion of Amino Acids 6 and 7

In the next step, the 5' portion of the mutated v-sis gene was replaced with a synthetic DNA fragment which changed amino acids 6 and 7 from the v-sis to the human PDGF B forms. This synthetic fragment also provided a translation-initiating ATG codon immediately preceding the codon for serine 1 of human PDGF B, as well providing sequences for binding to *E. coli* ribosomes and a restriction site for ligation into the desired *E. coli* expression vector (described below). The synthetic DNA fragment was ligated to the BglII site located at nucleotide 4061 of the v-sis gene (numbering system of Devare et al, ibid). Because a BglII site which is present within the M13mp19 vector would complicate and interfere with this step, the mutated v-sis gene was first moved to the commercially available plasmid vector pUC18, which does not contain a BglII site. The M13mp19/v-sis mutant RF DNA was restricted with SalI and BamHI, and the resulting 1193 base pair fragment isolated by electrophoresis using a low-melting temperature agarose gel. This fragment was ligated to the plasmid pUC18 which had also been restricted with SalI and BamHI. The ligated DNA was transformed into the commercially available *E. coli* K12 strain DH5 and transformants were selected by growth in the presence of ampicillin. Colonies were selected, grown in liquid culture, and isolated plasmid DNA analyzed by restriction mapping for the presence of the v-sis insert.

The pUC18/v-sis mutant DNA was restricted with HindIII, which cuts in the polylinker of pUC18 just upstream of the mutated v-sis insert, and with BglII, which cuts within the v-sis DNA at nucleotide 4061 (numbering system of Devare et al, ibid) corresponding to amino acid number 24 of the mature protein product. The large 3565 base pair fragment resulting from this reaction was isolated by electrophoresis in a low-melting temperature agarose gel. This fragment was ligated to a synthetic double-stranded DNA fragment with the following sequence:

```
5'AGCTTCTAGAAGGAGGAATAACATATGTCTCTGGGTTCGTTAACCATTGCG-
3'       GATCTTCCTCCTTATTGTATACAGAGACCCAAGCAATTGGTAACGC-

-GAACCGGCTATGATTGCCGAGTGCAAGACACGAACCGAGGTGTTCGA      3'
-CTTGGCCGATACTAACGGCTCACGTTCTGTGCTTGGCTCCACAAGCTCTAG 5'
```

This synthetic DNA fragment contains a HindIII "sticky" end at its upstream (left) end and a BglII "sticky" end at its downstream (right) end. In addition, an XbaI site (TCTAGA) is present within the synthetic DNA just downstream of the HindIII "sticky" end, which allows subsequent restriction with XbaI for ligation into the XbaI site of an expression vector described below. The ligated DNA was transformed into *E. coli* K12 strain DH5, with transformants being selected by growth on ampicillin-containing medium. The plasmid DNAs from resulting colonies were analyzed by restriction mapping for the presence of the synthetic DNA fragment. At this point, the pUC18/v-sis construction contained a mutated v-sis gene, with amino acid numbers 6, 7, 101, and 107 changed to the human PDGF B form, and its 5' end altered to begin translation with an ATG codon immediately preceding Serine 1.

Conversion of Amino Acid 114 and Placement of Stop Codon at Amino Acid 120

In the next step, the codon for amino acid number 114 was changed from ACT to GGT, resulting in the substitution of glycine for threonine in the final protein product. In addition, codon number 120, in which GCC codes for alanine in v-sis, was changed to TAA, a translation termination codon. The resulting protein product of this construction ends with the arginine at residue 119. Both of the changes were accomplished in one step by insertion of a synthetic DNA fragment after a SmaI site located within codon number 112.

The pUC18/v-sis mutant DNA generated above was restricted with SmaI, which cuts at nucleotide 4324 in the v-sis sequence (numbering system of Devare et al, ibid), and with EcoRI, which cuts in the polylinker of pUC18 just downstream of the v-sis insert. A small fragment (510 base pairs) between the SmaI and EcoRI sites, coding for the C-terminal portion of the v-sis protein and a 3' untranslated sequence, was removed by electrophoresis on a low-melting temperature agarose gel. The large fragment (about 3530 base pairs) was ligated to a synthetic DNA fragment having the following sequence:

```
5'GGGGGGTTCCCAGGAGCAGCGATAAG      3'
3'CCCCCCAAGGGTCCTCGTCGCTATTCTTAA 5'
```

The GGT codon coding for the new glycine residue at position 114 and the TAA termination codon introduced at position 120 are underlined above. This synthetic DNA fragment contains a blunt end at its upstream (left) end for ligating to the blunt end created by restriction of the v-sis mutant sequence with SmaI, and an EcoRI "sticky" end at its downstream (right) end for ligating to the EcoRI end created by restriction of the pUC18 polylinker with EcoRI. The ligated DNA was transformed into *E. coli* K12 strain DH5, with transformants being selected by growth on ampicillin-containing medium. The plasmid DNAs from resulting colonies were analyzed for the presence of the synthetic DNA fragment by restriction mapping.

Expression of PDGF B$_{119}$

In the final step, the completed form of the mutated v-sis gene was removed from pUC18 and ligated into the *E. coli* expression vector pCFM1156. The plasmid pCFM1156PL is prepared from the known plasmid pCFM836. The preparation of plasmid pCFM836 is described in U.S. Pat. No. 4,710,473, the relevant portions of the specification, particularly examples 1 to 7, are hereby incorporated by reference. To prepare pCFM1156 from pCFM836, the two endogenous NdeI restriction sites are cut, the exposed ends are filled with T4 polymerase, and the filled ends are blunt-end ligated.

The resulting plasmid is then digested with ClaI and KpnI and the excised DNA fragment is replaced with a DNA oligonucleotide of the following sequence:

```
  ClaI                                                              KpnI
-5'CGATTTGATTCTAGAAGGAGGAATAACATATGGTTAACGCGTTGGAATTCGGTAC3'
 3'    TAAACTAAGATCTTCCTCCTTATTGTATACCAATTGCGCAACCTTAAGC       5'
```

The pCFM1156 vector contains a region for insertion of foreign genes between an upstream XbaI site and one of a number of downstream restriction sites. In this case, the downstream EcoRI site was utilized. The pUC18/v-sis mutant DNA generated above was restricted with XbaI and EcoRI, with the small 383 base pair fragment being isolated by electrophoresis on a low-melting temperature agarose gel. This fragment was ligated to pCFM1156 DNA which had also been restricted with XbaI and EcoRI. The ligated DNA was transformed into *E. coli* K12 strain FM5 (ATCC #67545), with transformants being selected by growth on kanamycin-containing medium. The plasmid DNAs from resulting colonies were analyzed for the presence of the inserted DNA fragment by restriction mapping.

The final expression plasmid contained an inserted DNA sequence which codes for a protein that begins with an initiating methionine, followed by amino acids 1–119 of the human PDGF B chain sequence. The procaryotic *E. coli* host cells removed the N-terminal methionine after synthesis, so that the final protein produced corresponds to amino acids 1–119 of human PDGF B.

Expression of the 119 amino acid PDGF B protein was confirmed by growing bacterial cells containing the expression plasmid at 28°–30° C. until the desired optical density of the culture was reached, and then shifting the culture to growth at 42° for several hours. Samples of the cultured cells were taken prior to shifting to 42° C., and at several time points thereafter. It was observed, upon SDS-polyacrylamide gel electrophoretic analysis of the bacterial proteins, that a prominent band of apparent molecular weight 14.6 kd was present in temperature-induced, but not pre-induced, bacterial cells. This protein was present at an approximate level of 25-40 mg per liter of bacterial culture grown to an optical density at 600 nm of 1.0.

EXAMPLE 4

Confirmation of Primary Structure of E. coli rPDGF $B_{119}$

In order to confirm the expected amino acid sequence and homogeneity of the E. coli-produced PDGF $B_{119}$, the recombinant product from three different lots was purified from the inclusion bodies using known techniques, as more fully described in Example 5, and then analyzed by analytical gel electrophoresis and by protein sequencing.

Amino Acid Sequence Analysis

Amino acid sequence analysis was preformed as described in Example 2. This analysis confirmed that the rPDGF $B_{119}$ product from the E. coli host cells exhibited the expected sequence, which is shown in FIG. 1.

Analytical Gel Electrophoresis

The purified E. coli rPDGF $B_{119}$ from Example 3 was subjected to SDS-PAGE analysis under both reduced (5% 2-mercaptoethanol with heating) and unreduced (without heating) conditions. Electrophoretic analysis was carried out generally as described in Example 2, with the exception that samples were run on a 3 to 27% polyacrylamide gel alongside molecular weight standards obtained from Bio Rad Laboratories (Richmond, Calif.).

FIG. 4 shows the results for lots 1, 2, and 3 following staining with Coomassie Brilliant Blue. At sample loads of 3 to 24 μg, the only bands detected were those attributable to the E. coli rPDGF $B_{119}$. Under non-reducing conditions, a band was observed at approximately 30,000 mw. Upon reduction, a band was observed with an apparent mw of approximately 15,000.

EXAMPLE 5

Refolding of rPDGF B Chain Homodimer from E. coli Inclusion Bodies Using Glutathione as Blocking Agent Approximately 1.5 to 1.6 kg of harvested (i.e., concentrated) E. coli paste from Example 3, containing rPDGF $B_{119}$, was removed for refolding. The E. coli paste was suspended in 9 volumes (v/w) of 20 mM disodium ethylene diamine tetraacetic acid (EDTA), with the temperature being maintained at 4° C. The suspended cell paste was lysed using a Menton-Gaulin homogenizer at a pressure of 14,000 psi and a temperature of 12° C. The lysate was immediately centrifuged at 3,600×G for 60 minutes at 4° C. and the supernatant discarded, with the inclusion body rPDGF-containing pellet being saved.

The pellet was suspended in 14 volumes (v/w) of 8.5 M urea, 0.1 M glycine, pH 3.0, and stirred for 30 minutes. Meanwhile, SE Sepharose ® (Pharmacia) chromatography resin was drained by placing the commercially available resin in a scintered glass funnel, allowing the resin to drain by gravity, washing the resin with deionized water, and allowing the resin to drain once again. With continued stirring of the resuspended pellet, 2.4 kg of the drained resin was added to the pellet suspension. Stirring was stopped after 30 minutes. The resin was allowed to settle and the supernatant discarded. Five liters of 8.5 M urea, 0.1 M glycine, pH 3.5, was added to the settled resin. The mixture was stirred for an additional 5 minutes, with the resin again being allowed to settle, and the supernatant being discarded.

Five liters of 8.5 M urea, 20 mM phosphoric acid, pH 3.0, were then added to the settled resin. The resulting mixture was again stirred for 5 minutes, with the resin again being allowed to settle, and the supernatant being discarded. A second 5 liter volume of 8.5 M urea, 20 mM phosphoric acid, pH 3.0, was added to the settled resin. This mixture, with stirring, was subjected to a vacuum equal to 25 inches of mercury for 30 minutes. The vacuum was then broken, and the mixture was made 5 mM in dithiothreitol (DTT), with the pH being adjusted to 7.7 with 10 M sodium hydroxide (NaOH). The vacuum was restored and the mixture stirred for 30 minutes. Still under vacuum, with stirring discontinued, the resin was allowed to settle and 90% of the supernatant discarded. The resin was immediately slurried with the residual liquid and poured into a 25 cm diameter column (batch column), the flow adapter attached, and the resin packed at 100 cm/hour for 10 minutes with 8.5 M urea, 20 mM sodium phosphate ($Na_2HPO_4$), pH 7.7 that had been and was being sparged with $N_2$ gas (buffer A). The flow adapter was lowered to the surface of resin and the column washed with additional buffer A at a flow rate of 25 cm/hour until the effluent absorbance at 280 nm was constant.

The outlet of the batch column was then connected to the inlet of a second 25 cm×20 cm column (resolving column) packed with fresh SE Sepharose ® (Pharmacia) and equilibrated with buffer A. The batch and resolving columns were then resolved at a flow rate of 25 cm/hour with an 80-liter linear gradient from 100% buffer A to 100% buffer B (8.5 M urea, 20 mM $Na_2HPO_4$, 0.4 M NaCl, pH 7.7) which had been and was being sparged with $N_2$ gas. The appropriate fractions were immediately pooled and placed under vacuum as they came off the column. Yield was between 0.45 and 0.90 gm per liter of fermentation broth.

The denatured rPDGF $B_{119}$-containing solution was diluted, if necessary, to an absorbance of between 0.4 and 0.5 O.D. The protein solution was then made 0.1 M in oxidized glutathione and the pH adjusted to 8.0 with 10 M NaOH. The solution was again placed under vacuum and stirred for 18 to 24 hours. The vacuum was broken and the pH of the now derivatized rPDGF mixed disulfide intermediate was lowered to 3.0 with HCl. The resultant solution was concentrated to ½ the initial volume, and then diafiltered first against four volumes of 8.5 M urea, 0.1 M acetic acid, and then followed by four volumes of 0.1 M acetic acid using an Amicon YM ® 10 (Amicon Inc., Danvers, Mass.) ultrafiltration membrane. The final protein concentration was between 15 1.5 and 2.0 mg/mL $$\left(\epsilon_{280nm}^{1\%} = 0.46\right)$$

rPDGF-S-S-G purity >85%, and yield of between 0.45 and 0.90 gm per liter of fermentation broth.

Refolding was effected by dilution of the rPDGF-S-S-G solution to 0.1 mg/mL with 20 mM Tris. Subsequently, 1 M cysteine in 0.1 M acetic acid was added to this solution, to a final concentration of 1 mM, and the pH adjusted to 8.0 with NaOH. The solution was allowed to stir for 16 hours, in order to unblock the derivatized rPDGF-S-S-G intermediate and initiate formation of intrachain and interchain disulfide bonds, and then made 0.1 M in acetic acid. Yield was 0.32 to 0.63 gm per liter of fermentation broth.

The refolded rPDGF solution was loaded, at a flow rate of 100 cm/hr, onto a 11.3×5 cm column of controlled pore glass (CPG, pg-350-400, 96 $M^2$/gm, 382 Å mean pore diameter, Sigma Chemical Company, St. Louis, Mo.), equilibrated in either 0.05 M glycine, pH 3.5 (buffer C) or 0.05 M glycine, 0.4 M NaCl, pH 3.5 (buffer D). Following the loading of the PDGF postoxidation solution onto the column, the column was washed with the equilibration buffer at a flow rate of 40 cm/hr. The purified PDGF was then eluted from the column, again at a flow rate of 40 cm/hr, by the application of a 5 liter gradient starting with either buffer C or D and finishing with either 2 M guanidine.HCl in buffer C or 8 M urea in buffer D.

The appropriate fractions of pure PDGF were pooled. The yield was between 0.25 and 0.5 gm per liter of fermentation broth.

EXAMPLE 6

Mitogenic Activity of Refolded rPDGF B Chain Homodimer

The refolded rPDGF $B_{119}$ homodimer from Example 5 was assayed for mitogenic activity by a thymidine uptake assay using normal rat kidney cells, Clone 49F, ATCC #CRL-1570 (NRK) by a modification of the method described by Pierce et al, *J. Exp. Med.*, 176, 974-987 (1988), using mammalian rPDGF B from CHO cells as a standard. The NRK cells were grown in a growth medium (FBS-DMEM) comprising: (1) Dulbecco's Modified Eagle Medium (DMEM), containing 1 g/L glucose, 1% (w/v) penicillin-streptomycin solution (100×, 10,00 units penicillin, 10,000 μg streptomycin/mL), and 1% (v/v) L-glutamine solution at 100×, 200 mM; and, (2) 7.5% Fetal Bovine Serum (FBS) (Whitaker MA Bioproducts, Walkersville, Md.).

Cells were plated into 24-well microtiter plates at a density of $2 \times 10^4$ cells/well in FBS-DMEM. After 5 days, the FBS-DMEM was aspirated and replaced with 1 mL of DMEM without FBS, in order to "starve" the cells so that they might respond more markedly upon exposure to PDGF. The cells were incubated in this medium for 24 hours, after which time, 50 μL of a PDGF-containing sample was added to each well. After a further 18 hour incubation, the PDGF-containing sample was aspirated and replaced with 1 mL of labeling medium consisting of DMEM, 5% FBS, and 2 μCi/mL of $^3$H-thymidine. The plates were incubated for an additional 1 hour at 37° C. Cells from triplicate wells were detached with a sucrose/EDTA solution and harvested with an automated microharvester onto glass fiber filter mats. The cells were fixed onto the mats with ethanol, and after drying, the mats were counted in a scintillation counter.

Figure 5:
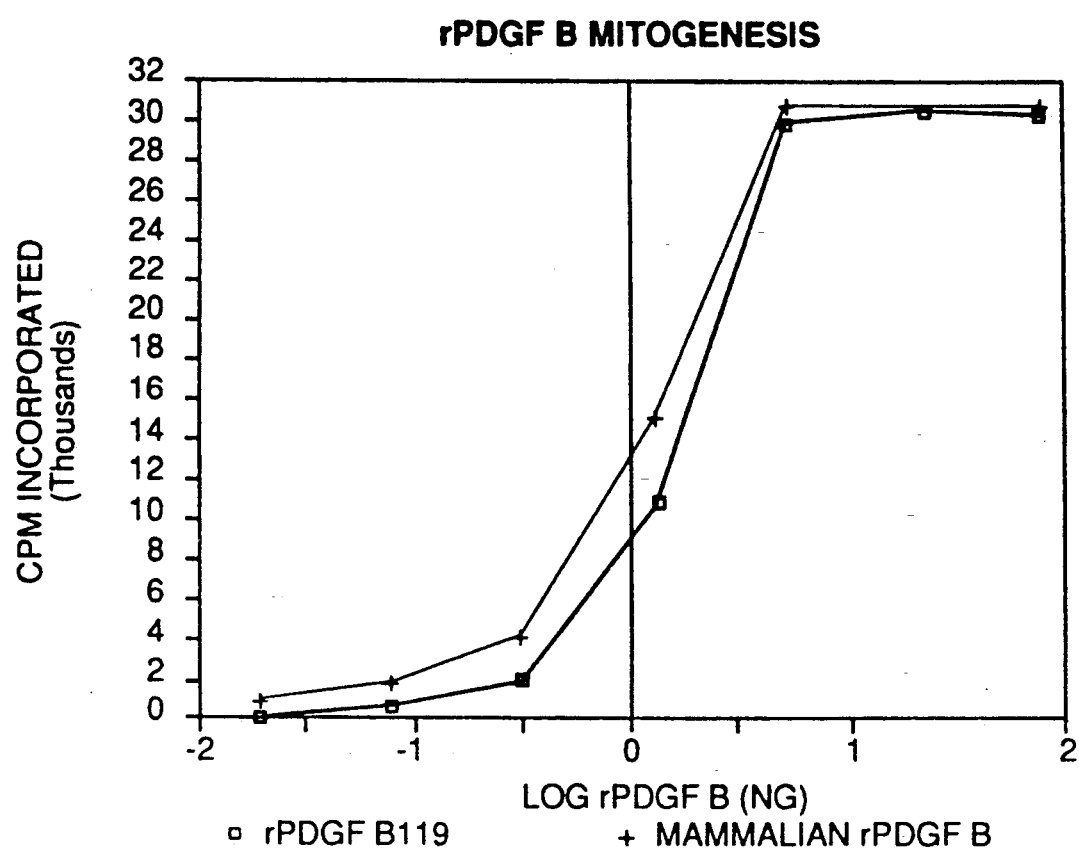
FIG. 5 is a graph showing the mitogenic activity of *E. coli*-produced rPDGF $B_{119}$ which has been refolded in accordance with the teachings of the present invention.

The average value of control wells receiving no PDGF was subtracted from the averaged triplicate counts of each experimental sample. The log of the PDGF concentration in ng/mL was plotted vs. cpm incorporated for each sample. The results are set forth in FIG. 5. These results demonstrate that the refolded rPDGF $B_{119}$ from Example 5 has substantially the same mitogenic activity as the rPDGF B from the eucaryotic CHO host cells.

EXAMPLE 7

Chemotactic Activity of Refolded rPDGF B Chain Homodimer

The refolded rPDGF $B_{119}$ homodimer from Example 5 was also assayed for chemotactic activity on fibroblasts and monocytes essentially as described in Senior et al, *J. Cell. Biol.*, 96, 382-385 (1983); Deuel et al, *J. Clin. Invest.*, 69, 1046-1049 (1982). The rPDGF $B_{119}$ from Example 4 was tested in Boyden chambers as described in the referenced articles, using mammalian rPDGF B from CHO cells as a standard. In this test, cells migrate through a filter, from one chamber without a chemotactic agent to another chamber with a chemotactic agent. After a given period of time, the number of cells in a microscopic field on the side with the chemoattractant are counted.

Fibroblasts were obtained from explants of normal adult skin surgical specimens. The cells were cultured in Dulbecco's modified Eagle's medium (DMEM), supplemented with 2 mM L-glutamine, nonessential amino acids, and 10% fetal bovine serum (KC Biological, Inc., Lenexa, Kans.). The cells were used for assays after six passages. Human blood mononuclear cells (monocytes) were obtained using Ficoll/Hypaque gradients, and suspended in DMEM supplemented with 2% human albumin at densities of $2.5 \times 10^6$ cells/mL.

Chemotaxis was determined in a multi-blind well apparatus having 30 wells. A double-membrane technique, using a polycarbonate membrane (Nucleopore Corporation, Pleasanton, Calif.) with 8 μm pores (fibroblasts) or 5 μm pores (monocytes) on top of a cellulose nitrate membrane (Millipore Corporation, Bedford, Mass.) having 0.45-μm pores, was used to separate each well into an upper and lower compartment. The lower compartment was filled with either PDGF solution to be assayed, or control medium, then covered with the membranes, in the appropriate order, after which a cell suspension containing fibroblasts or monocytes was added to the upper compartment. After both compartments of the wells were filled, the chemotaxis apparatus was placed in a humidified incubator at 37° C. in an atmosphere of 5% carbon dioxide/95% air for 6 hours. The apparatus was then disassembled and each membrane pair was removed and stained.

Figure 6:
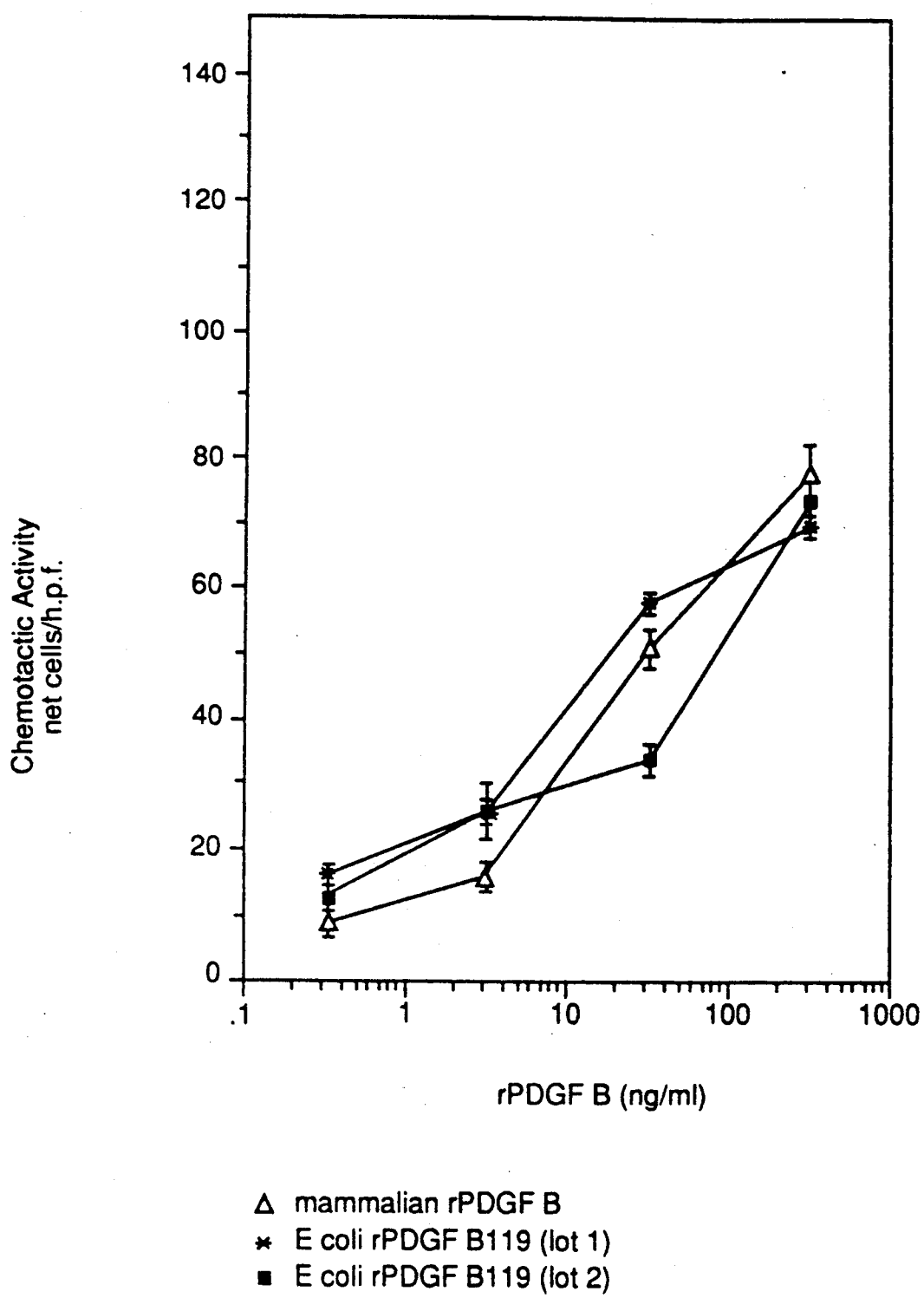
FIG. 6 is a graph showing the chemotactic activity on fibroblasts of *E. coli*-produced rPDGF $B_{119}$ which has been refolded in accordance with the teachings of the present invention.
Figure 7:
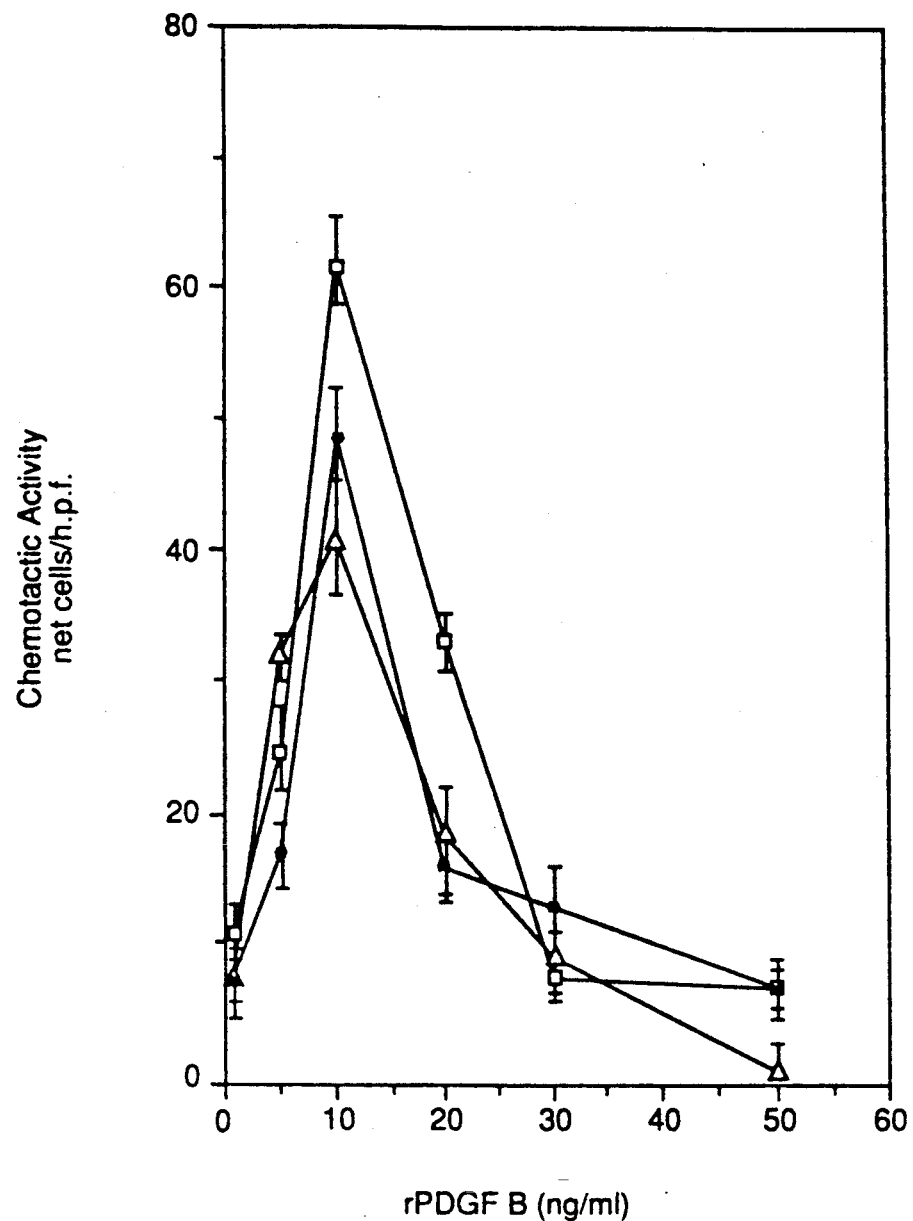
FIG. 7 is a graph showing the chemotactic activity on monocytes of *E. coli*-produced rPDGF $B_{119}$ which has been refolded in accordance with the teachings of the present invention.

Cell migration was determined by counting, under high power magnification (×400), the cells that had moved to the interface between the two membranes and those on the lower membrane. Five high-power fields (hpf) were counted per membrane pair. Cell migration is expressed as the net number of cells migrated per hpf, that is, the number of cells per hpf minus the number of cells per hpf that migrated in response to control medium. The results from the chemotaxis assay on fibroblasts is shown in FIG. 6 and on monocytes in FIG. 7. These results show the refolded rPDGF $B_{119}$ from Example 5 to have substantially the same chemotactic activity as the rPDGF B from the eucaryotic CHO host cells.

What is claimed is:

1. A recombinant protein having a homogeneous amino acid sequence comprising amino acids 1-119 of PDGF $B_{109}$ precursor protein.

2. The recombinant protein of claim 1 having the amino acid sequence 1-119 set forth in FIG. 3

3. A pharmaceutical composition comprising a therapeutically effective amount of the homogeneous recombinant protein of claim 1 and a pharmaceutically acceptable carrier.

4. The pharmaceutical composition of claim 3 wherein said homogeneous recombinant protein has the amino acid sequence 1-119 set forth in FIG. 3.

* * * * *